(12) United States Patent
Cotta et al.

(10) Patent No.: US 9,732,312 B2
(45) Date of Patent: Aug. 15, 2017

(54) METHOD AND DEVICE FOR FEEDING GASES OR GAS MIXTURES INTO A LIQUID, SUSPENSION OR EMULSION IN A REACTOR IN A SPECIFIC MANNER

(75) Inventors: Fritz Cotta, Merseburg (DE); Jochen Grossmann, Dresden (DE); Martin Matschke, Greiz (DE); Andreas Koetz, Dessau-Rosslau (DE)

(73) Assignee: Gicon Grossmann Ingenieur Consult GmbH, Dresden (DE)

( * ) Notice: Subject to any disclaimer, the term of this patent is extended or adjusted under 35 U.S.C. 154(b) by 276 days.

(21) Appl. No.: 14/236,910

(22) PCT Filed: Aug. 31, 2012

(86) PCT No.: PCT/EP2012/066965
§ 371 (c)(1),
(2), (4) Date: Feb. 4, 2014

(87) PCT Pub. No.: WO2013/030340
PCT Pub. Date: Mar. 7, 2013

(65) Prior Publication Data
US 2015/0056685 A1    Feb. 26, 2015

(30) Foreign Application Priority Data
Sep. 1, 2011    (DE) .......................... 10 2011 081 979

(51) Int. Cl.
*C12M 1/00*    (2006.01)
*C12N 1/12*    (2006.01)
(Continued)

(52) U.S. Cl.
CPC ......... *C12M 21/02* (2013.01); *B01F 3/04106* (2013.01); *C12M 29/06* (2013.01);
(Continued)

(58) Field of Classification Search
CPC ...... C12M 29/12; C12M 21/02; C12M 29/06; C12M 39/00; C12M 29/18; C12M 29/26;
(Continued)

(56) References Cited

U.S. PATENT DOCUMENTS 4,184,481 A * 1/1980 Tornquist .................. F24J 2/05
126/585
4,481,292 A * 11/1984 Raymond ............... C07C 45/86
435/147

(Continued)

FOREIGN PATENT DOCUMENTS

AU    2006100045 A4 *  2/2006  ............ C12M 21/02
CN        101724549 A      6/2010
(Continued)

*Primary Examiner* — Amber R Orlando
*Assistant Examiner* — Stephen Hobson
(74) *Attorney, Agent, or Firm* — Michael Soderman

(57) ABSTRACT

The invention relates to a method and to a device for feeding gases or gas mixtures into a liquid, suspension, or emulsion in a reactor in a specific manner. According to the invention, gases or gas mixtures are fed into a liquid, suspension, or emulsion in a reactor in a specific manner, wherein the gas or gas mixture is fed in a specific amount and/or at defined points in time in one pulse as a gas bubble into a flowing liquid in a tilted reactor system, whereby a pulsation effect is obtained, wherein a driving force is produced by means of an adiabatic relaxation of the fed-in gas or gas mixture, by means of which driving force wall adhesions on the reactor are prevented.

11 Claims, 3 Drawing Sheets

(51) Int. Cl.
*B01F 3/04* (2006.01)
*C12M 1/107* (2006.01)

(52) U.S. Cl.
CPC ............ *C12M 29/12* (2013.01); *C12M 39/00* (2013.01); *C12N 1/12* (2013.01); *B01F 2215/0073* (2013.01); *C12M 23/36* (2013.01); *C12M 29/18* (2013.01); *C12M 29/24* (2013.01); *C12M 29/26* (2013.01)

(58) Field of Classification Search
CPC .... C12M 29/24; C12M 23/36; B01F 3/04106; B01F 2215/0073
See application file for complete search history.

(56) References Cited

U.S. PATENT DOCUMENTS

| | | | | |
|---|---|---|---|---|
| 4,649,117 | A * | 3/1987 | Familletti | B01F 13/0255 435/296.1 |
| 4,992,370 | A * | 2/1991 | Kalina | C12M 21/12 435/161 |
| 5,503,750 | A * | 4/1996 | Russo, Jr. | C12M 47/10 210/259 |
| 5,585,266 | A * | 12/1996 | Plitt | C12M 23/52 210/150 |
| 5,846,828 | A * | 12/1998 | Peterson | A61F 2/062 435/284.1 |
| 5,916,800 | A * | 6/1999 | Elizondo | A01N 1/00 435/284.1 |
| 6,220,822 | B1 * | 4/2001 | Khudenko | F04F 1/18 417/54 |
| 7,629,167 | B2 * | 12/2009 | Hodge | B01F 13/0827 366/274 |
| 2001/0051371 | A1 * | 12/2001 | Kiplinger | C12M 23/02 435/262 |
| 2005/0064577 | A1 * | 3/2005 | Berzin | B01D 53/85 435/266 |
| 2005/0098497 | A1 * | 5/2005 | Khudenko | B01D 19/0031 210/620 |
| 2005/0239182 | A1 * | 10/2005 | Berzin | C12M 21/02 435/166 |
| 2005/0260553 | A1 * | 11/2005 | Berzin | B01D 53/85 435/3 |
| 2008/0160591 | A1 * | 7/2008 | Willson | C12M 21/02 435/132 |
| 2008/0185336 | A1 * | 8/2008 | Maekawa | B09B 3/00 210/603 |
| 2008/0286851 | A1 * | 11/2008 | Whitton | C12M 21/02 435/243 |
| 2008/0293132 | A1 * | 11/2008 | Goldman | C12M 21/02 435/292.1 |
| 2009/0011492 | A1 * | 1/2009 | Berzin | B01D 53/84 435/257.1 |
| 2009/0269812 | A1 * | 10/2009 | Sawai | C12P 13/04 435/88 |
| 2009/0303829 | A1 * | 12/2009 | Muecke | B01F 3/0451 366/101 |
| 2011/0086386 | A1 * | 4/2011 | Czartoski | C12N 1/06 435/67 |
| 2011/0092726 | A1 * | 4/2011 | Clarke | C12M 21/02 554/175 |
| 2011/0151507 | A1 * | 6/2011 | van Walsem | C12M 21/02 435/41 |
| 2011/0177551 | A1 * | 7/2011 | Mimitsuka | C12M 29/18 435/41 |
| 2011/0244543 | A1 * | 10/2011 | Larsen | B01J 19/006 435/170 |
| 2012/0202282 | A1 * | 8/2012 | Hinkens | C12M 23/22 435/292.1 |
| 2012/0202290 | A1 * | 8/2012 | Mueller-Rees | C12M 21/02 435/410 |

FOREIGN PATENT DOCUMENTS

| | | |
|---|---|---|
| DE | 1233129 B | 1/1967 |
| JP | 1300021 A | 12/1989 |
| WO | 02099032 A1 | 12/2002 |
| WO | 03094598 A1 | 11/2003 |
| WO | 2009149519 A1 | 12/2009 |
| WO | 2010125199 A2 | 11/2010 |
| WO | 2011022349 A1 | 2/2011 |
| WO | 2011048108 A2 | 4/2011 |
| WO | WO 2012010612 A1 * | 1/2012 ............ C12M 21/02 |

* cited by examiner

METHOD AND DEVICE FOR FEEDING GASES OR GAS MIXTURES INTO A LIQUID, SUSPENSION OR EMULSION IN A REACTOR IN A SPECIFIC MANNER

CROSS REFERENCE TO RELATED APPLICATIONS

This application is the U.S. national stage of International Application No. PCT/EP2012/066965 filed on Aug. 31, 2012, and claims the benefit thereof. The international application claims the benefit of German Application No. 102011081979.1 filed on Sep. 1, 2011; all applications are incorporated by reference herein in their entirety.

BACKGROUND

The invention relates to a method and a device for feeding gases or gas mixtures into a liquid, suspension or emulsion in a reactor in a specific manner.

Carbon dioxide arises as a waste product in a number of technical processes, especially during the combustion of fossil fuels (coal and coke) with excess air, during the burning of lime or during the production of synthesis gas (gasification of coal and steam reforming). The synthesis gas is washed, for instance according to the Rectisol method, for use in the synthesis of ammonia or methanol as an example; carbon dioxide can be recovered in a very pure form in the process. Carbon dioxide is compressed, liquefied or frozen and precipitated in the form of dry ice at the production site for easier transport.

Although there are a few possibilities for the use of carbon dioxide, e.g. in the food industry (dry ice cooling, carbonated beverages and carbonic maceration), in the chemical industry (urea synthesis and the Kolbe-Schmitt reaction to form salicylic acid), during welding as a protective gas or for use in fog machines, consumption is significantly less than the amount produced. Methods for the use of carbon dioxide in efficient materials management above all have become more important in the last few years because of the increasing climate change caused by the greenhouse gas carbon dioxide and the increasing global population. The production of micro-algae is currently the most promising method for materials-management or energy-related use because of the approximately 100 times greater creation rate of biomass compared to terrestrial plants. Biomass, which can be used in a variety of applications (e.g. carotenoids, lipids and/or proteins), is created via photosynthesis from carbon dioxide, water and (sun)light.

A number of photobioreactors and process concepts have been developed throughout the world up to now; the closed photobioreaction system has increasingly gained acceptance because the entry of germs, fungi, bacteria and similar contaminants in it is virtually ruled out. In the area of closed systems, flow-through tube systems, especially double tube systems, demonstrate significant advantages with regard to dead flow zones, bio-film buildup, rotting, cleaning times, energy efficiency, heat transfer, heat control and biomass growth vis-a-vis plate or bag systems. What has been common to all closed systems up to now is the addition of carbon dioxide or gases containing carbon dioxide (smoke gas) from pressure containers or pressurizing units, for instance compressors and blowers. Carbon dioxide is exclusively used in terms of material-management aspects. The reaction system is cooled by means of a separate cooling circuit in small systems (the temperature of the cooling water is controlled by thermostats, for instance) and by means of evaporation cooling, as an example, in large systems (water is sprayed onto the photobioreaction system). Bio-film buildup on the walls of the reactor is a problem with regard to photobioreactors that has not been solved up to now; fairly long standstill periods of the system result from that because of shorter cleaning intervals, and there are lower biomass growth rates up to a possible complete loss of the biomass because of rotting processes.

Furthermore, a biomass dry weight content of approx. 5 g/l is achieved in customary photobioreactors at present. Flocculation and settling take place on the reactor walls with higher concentrations, which leads to a situation in which light can no longer get into the interior of the reactor.

This effect is counteracted by the use of high flow velocities, which requires the use of greater pumping power. In addition, abrasive cleaning particles are added to the system. They substantially increase the technical effort for suspension separation and simultaneously minimize the photoactive reaction volume.

This procedure for achieving efficient production methods is absolutely necessary in the case of micro-algae production. Otherwise, cellular respiration (dark reaction) increasingly takes place instead of the desired photosynthesis (light reaction), which can lead to the death of the culture in the end. A limitation of the maximum biomass dry weight concentration to approx. 5 g/l also follows from the amount of energy required to thoroughly mix the system to supply sufficient light to all of the micro-algae. Furthermore, a small concentration of micro-algae in the suspension requires a substantial amount of energy for the separation and drying of the micro-algae. An efficient procedure for the production of micro-algae therefore brings about the necessity of higher concentrations of the biomass dry weight before the treatment processes.

A number of reactions to create products are used in the material-transformation industry that have the prerequisite of an intensive mixing of the reactants, especially when gases are used in liquids. These operating processes frequently require the use of complicated technical systems or they are associated with a great deal of energy use. Systems of that type especially have critical requirements in biotechnology, where contamination-free or low-contamination operating processes are important. As an example, photobioreactors require elaborate systems to minimize the bio-film buildup at the areas where light enters and to consequently ensure on the whole that there is production of biomass over time periods of several weeks. Various methods are known with regard to this in the prior art:

For example, U.S. Pat. No. 6,220,822 B1 describes an airlift reactor that is essentially comprised of a pipe filled with a liquid into which air can be blown. The air bubbles ascend through the pipe into a discharge port and come up against a tilted baffle in this port. A flow of the liquid in the discharge port is forced in the same direction because of the upwards movement of the gas bubbles on the surface of the baffle. In addition to baffles, conical parts are also proposed that likewise bring about a flow in the discharge port.

U.S. Pat. No. 4,649,117 describes a reactor that uses the airlift principle, for instance, for a more effective harvest of cells from fermenters/bioreactors. Optimal circulation of the liquid without the use of mechanical stirring units with a minimum of mechanical shearing force is described as the essential advantage of this application. The compressed gas that is used consists of air with a share of carbon dioxide of approximately 5%. As per the invention, the gas bubbles fed in at the base of the reactor go straight upwards. The reactor content is around 5-7 liters.

Furthermore, US 2009/0303829 A1 discloses the use of a flexible, double-walled, inflatable plastic sheeting in the form of a tube for feeding in air that is anchored in the middle of the base of the storage container. The gases that are supplied could be air, oxygen, carbon dioxide or other gases.

WO 99/25657 describes a bioreactor with good mixing for the aerobic treatment of aqueous waste with a high proportion of organic and solid components using the airlift principle. In addition to the "airlift pump", a diffuser is also employed to distribute the gases that are used, e.g. oxygen, nitrogen and ammonia. WO 99/25657 exclusively describes the treatment of aqueous waste; the gases that are used are converted via redox reactions.

U.S. Pat. No. 7,629,167 B2 discloses flexible, disposable bioreactors in the form of containers/bags/sacks made of plastic. The flexible and exchangeable bioreactor is surrounded by a solid vessel, for instance a tank, in the process. Various fittings/connectors are described for the exchange of liquids and/or gas. Moreover, sensors can be used to monitor the bioreactor. Baffles or other parts over the gas inlet opening can be used to generate flows in the bioreactor. (Condensed/pumped) gases that are used could be air, oxygen and/or carbon dioxide.

US 2005/0098497 A1 describes a reactor that is essentially characterized in that it is filled with a liquid or suspension. If there is a suspension, a gas is supplied via an immersed pipe and distributed via diffusors, so the density of the liquid-gas mixtures is substantially lowered and the solid settles. The application possibilities of a separation of solids and liquids that are stated in US 2005/0098497 A1 result from that. The separation effect is increased by the fact that the gas can be added in a pulsating fashion. Furthermore, various modifications (installation of filters/packed bed into the reactor, baffles and various diffusor geometries) are cited.

WO 2011/048108 A2 describes a tube photobioreactor, e.g. for the production of micro-algae, with a truncated-cone-shaped core structure and one or more transparent or translucent tubes. The tube is wound onto the base frame in a helical fashion and particularly distinguishes itself by the fact that it has at least two chambers. A cultivation medium flows through at least one chamber, and a heat-exchange medium flows through at least one chamber. The tube material is made of plastic or glass, preferably silicones. The bio-film buildup and therefore the system standstill periods because of cleaning work are minimized because of that. The conveyance of the cultivation medium takes place in the tube by means of an airlift in the process, i.e. takes place by means of air or by means of an air-$CO_2$ mixture or nitrogen as a carrier gas, which simultaneously ensures the supply of the cultivation medium with $CO_2$. The airlift principle is based on the feed-in of finely distributed gases (airlift pump). But the supply of $CO_2$ or gases containing $CO_2$ can also take place, separately and pulsed, via a combined system or in the upstream area of the pump and therefore serve to set the pH value in the cultivation medium.

The regulation of the pH value by the gases that are used requires a large surface area of the phase boundaries between them and the liquid, however, which has the prerequisite of a gas that is distributed as finely as possible in accordance with the prior art.

The prior art has the drawback, in addition to the limited biomass concentration of approx. 5 g/l due to bio-film buildup, that corresponding cleaning efforts and therefore reactor standstill periods or increased effort to separate the biomass dry weight, for instance when abrasive cleaning particles are added, is necessary.

A method that ensures an increase in the concentration of the biomass dry weight over 5 g/l and a simultaneous reduction of the bio-film buildup in a simple way, and consequently a reduction in the standstill periods of bioreactors, would be extremely desirable.

The task of this invention therefore consists in describing a method that overcomes the drawbacks in the prior art and that makes an increase in the biomass concentration over 5 g/l possible in a simple way with a simultaneous reduction in the bio-film buildup.

DETAILED DESCRIPTION

The problem is solved by a method in accordance with Claim 1. Advantageous design forms are provided in the dependent claims.

As per the invention, the problem is solved with a method for feeding gases or gas mixtures into a liquid, suspension or emulsion in a photobioreactor in a specific manner. In so doing, the gas or gas mixture is fed in with a specific amount and/or at defined points in time; a pulsation effect is obtained in the process. A propulsive force is created because of that via an expansion of the fed-in gas or gas mixture; heavy turbulence is generated in the process in the liquid, suspension or emulsion because of the propulsive force that is obtained, and material is prevented from clinging to the walls of the photobioreactor. The turbulence that is generated in that way in the liquid, suspension or emulsion consequently makes a thorough mixing of the dissolved components and the solids possible. An expansion of the fed-in gas or gas mixture as defined by this patent application means the cooling of the gas or gas mixture during the transition from an area of high pressure to an area of low pressure; the low temperature that arises in the process is used for cooling in accordance with the invention.

There is also a thorough mixing of the liquid, suspension or emulsion because of the pulsation that is generated in addition to the propulsive force that is continuously created in this way. The disadvantageous clinging of material to the walls in the reactor is prevented because of that. Pulsation as defined by this patent application is defined to mean the feeding of cycled gas flows or gas mixtures into flowing liquids, suspensions or emulsions. Compared with the prior art, the gas is not finely distributed in the process, but instead fed in as a gas bubble in one burst.

In a further embodiment of the invention, the liquid, suspension or emulsion is conveyed in a pulsating fashion. The pulsation effect arising due to the pulsating feed-in of the gas or gas mixture can be strengthened because of that when the liquid, suspension or emulsion is likewise conveyed in a pulsating fashion, e.g. with a diaphragm pump, for the feed-in of the gas. The turbulence arising in the liquid, suspension or emulsion can be effectively adjusted in this way in accordance with the requirements by adapting the feed-in of the gas or the pulsating conveyance of the liquid. A minimization of shearing forces can be realized because of that with a simultaneous maximum mixing of the liquid, suspension or emulsion.

In a further embodiment of the invention, the gas or gas mixture is fed in with a high internal energy. Internal energy as defined by this patent application is understood to mean the energy that the gas or gas mixture that is employed contains due to its compression and that can be converted into mechanical work, similar to the case of a gas or thermal engine.

In a further embodiment of the invention, the gas or gas mixture is used in a compressed, at least partially condensed or at least partially frozen form. The gas or gas mixture has greater internal energy compared to the normal state because of that. Moreover, the gas or gas mixture can also be used to cool the liquid, suspension or emulsion in addition to the creation of a pulsation effect.

In a further embodiment of the invention, the liquid, suspension or emulsion that is conveyed is cooled via complete or partial use of the internal energy of the fed-in gas or gas mixture. Cooling of the liquid, suspension or emulsion can also take place in an advantageous way via the fed-in gas or gas mixture in addition to the generation of a pulsation effect because of that. As a result, the feed-in of the gas or gas mixture makes a contribution towards both the material and the energy circulation system of the reactor.

In a further embodiment of the invention, the liquid is conveyed in a pulsating fashion via complete or partial use of the internal energy of the fed-in gas or gas mixture. In the process, the internal energy of the fed-in gas or gas mixture is used to operate a diaphragm pump, for instance, which brings about a pulsating conveyance of the liquid.

In a further design form of the invention, the internal energy of the gas or gas mixture is separately used, but preferably in a combined manner in a material and energy circulation system in the form of combined heat and power generation. Combined heat and power generation is understood in the energy sector, especially in power stations, to mean the simultaneous generation of mechanical energy that is directly converted into electrical power and useful thermal energy for heating purposes. The generation of mechanical work to operate the diaphragm pumps and the use of the vaporization/expansion heat via the gas or gas mixture that is used are understood in an analogous way as defined by this patent application.

In a further embodiment of the invention, the gas or gas mixture, after being fed into the liquid, suspension or emulsion, is partially or completely transformed in the liquid, suspension or emulsion and/or dissolved in the liquid, suspension or emulsion. This is particularly advantageous when the fed-in gas that brings about a pulsation of the liquid serves as a substrate for the microorganisms cultivated in the photobioreactor. So a gas or gas mixture containing $CO_2$, as an example, can be fed in for pulsation; this is metabolized by micro-algae in the light reaction of the photosynthesis to form $O_2$ for instance.

In a further embodiment of the invention, the gas or gas mixture is fed into a photobioreactor. A bioreactor for cultivating and producing phototrophic single or multi-cell organisms such as algae, cyanobacteria, moss or plant cell cultures is called a photoreactor or a photobioreactor.

In a further embodiment of the invention, the gas or gas mixture is fed into a photobioreactor with micro-algae. The term "algae" as broadly defined encompasses eukaryotic, plant-like organisms living in water that carry out photosynthesis, but that do not belong to actual plants. In a narrower sense, numerous protist groups are called that. Both microscopically small, one-cell organisms and multicell, sometimes giant organisms are among the algae types. As per the definition, only algae types with a single cell or a few cells, which are called micro-algae, are regarded as microorganisms. These micro-algae carry out photosynthesis, as do all algae; they use light as an energy source in the process and are carbon autotrophic. Further examples of carbon (photo-)autotrophic organisms are purple sulfur bacteria or green sulfur bacteria.

In a further embodiment of the invention, carbon dioxide is fed in. This is especially advantageous in the cultivation of micro-algae, because they can convert carbon dioxide into biomass. An environmentally friendly conversion of carbon dioxide with a simultaneous generation of biomass is possible because of that.

In a further embodiment of the invention, a gas or gas mixture including carbon dioxide is fed in. The fed-in gas mixture could involve smoke gas, for instance. The expansion heat generated by the adiabatic expansion can optionally be used in the process to cool down the cooling water when a double-tube system is used.

In a further embodiment of the invention, a further gas or gas mixture including carbon dioxide is fed in, in addition to the gas or gas mixture that is fed in for pulsation. The further gas or gas mixture including carbon dioxide serves as a substrate for the light reaction of the phototrophic microorganisms. The gas or gas mixture fed in for pulsation could, for example, be an inert gas or gas mixture, for instance air or a noble gas. The expansion heat generated by the adiabatic expansion can optionally be used in the process to cool down the cooling water when a double-tube system is used.

In one design form of the embodiment described above, the gas or gas mixture including carbon dioxide fed in for pulsation has a high internal energy and is used for the pulsating conveyance of the liquid by means of a diaphragm pump.

In an alternative design form of the embodiment described above, the gas or gas mixture fed in for pulsation has a high internal energy and is used for the pulsating conveyance of the liquid by means of a diaphragm pump. In addition, a further gas or gas mixture including carbon dioxide is fed into the photobioreactor. The further gas or gas mixture can be continuously added at a constant rate in the process.

In a further embodiment of the invention, the gas or gas mixture is fed in from the bottom of the reactor and rises vertically up through the liquid, suspension or emulsion opposite the direction of gravity. To develop the desired effect, the reactor, which is preferably designed in the form of a tube reactor, does not have a vertical design in contrast to the airlift principle, but instead a tilted design; the gas is not fed in with a finely distributed form, but instead in one burst in the form of a gas bubble. "Tilted" as defined by this invention is understood to mean a tube with an angle vis-a-vis the horizontal plane of $0°<\alpha<90°$, preferably $0°<\alpha<10°$, especially preferably $0°<\alpha<5°$, which is helically wrapped around a reactor frame with a truncated-cone design. Because the gas or gas mixture is fed in from the bottom of the reactor and it ascends in a tilted reactor system opposite the direction of gravity, dead zones are avoided in the reactor and an even, pulsating feed is therefore made possible; moreover, more precise control of the pulsation and therefore a turbulent mixing of the liquid, suspension or emulsion can be obtained because of that.

In a further embodiment of the invention, the flowing liquid, suspension or emulsion in the reactor is pumped through the photobioreactor opposite the direction of gravity at 0.35-0.50 m/s, preferably at 0.40 m/s. The flowing liquid, suspension or emulsion in the reactor is preferably pumped with a diaphragm pump in the process.

In a further embodiment of the invention, the amount of gas or gas mixture that is fed in with pulsation is 0.00-1.00 liters/s, preferably 0.00-0.10 liters/s, especially preferably 0.00-0.01 liters/s, under standard conditions (20° C., 101325 Pa) depending on the concentration of solids and/or the degree of contamination, preferably with an algae concentration of 6 g/l or more in the liquid, suspension or emulsion.

The subject matter of this invention also involves a method for suspending or emulsifying mixtures in a reactor; a propulsive force is generated by means of expansion of a fed-in gas or gas mixture. The propulsive force that is obtained in the process creates heavy turbulence in the liquid, suspension or emulsion; a gentle homogenization of the suspension or emulsion mixture that is efficient in terms of material and energy is advantageously achieved because of that. Strong turbulence as defined by the invention is understood to mean non-laminar, and thus turbulent flows (Re>2300) in the liquid, suspension or emulsion that are specifically strengthened by the gas input and that can therefore prevent material from clinging to the walls, for example, because of intensive (phase) mixing.

The method steps described above are especially advantageous for avoiding bio-film buildup in a reactor. The turbulence arising due to the feeding of gas into the reactor, for instance, prevents solid particles, microorganisms and the like from clinging to the walls in the reactor. Reactor standstill times and the required cleaning activities are therefore reduced to a minimal amount. At the same time, higher biomass dry weight concentrations can be achieved because microorganisms are prevented from clinging to the walls, which leads in the end to more effective process control with significantly higher space-time yields.

The problem is also solved with a device for carrying out the method described above. The device includes a reactor here; equipment for feeding in the gas or gas mixture is provided on the bottom of the reactor. The fed-in gas or gas mixture ascends through the liquid, suspension or emulsion opposite the direction of gravity because of that; because of the tilted arrangement of the reactor and the pulsed feeding of the gas without a fine distribution, a gas-bubble scenario arises causing the liquid to smash apart the gas spaces that form because of the abrupt backflow in the direction of gravity. As a result, turbulence is generated in the liquid, suspension or emulsion with a pulsating feed-in of the gas or gas mixture, which is why there is an intensive mixing of the liquid, suspension or emulsion. Consequently, bio-film buildup on the wall of the reactor is prevented. Moreover, a settling of solids or a phase separation is prevented because of the pulsating feed-in of the gas or gas mixture. Dead zones in the reactor are avoided and an even, pulsating feed-in is therefore made possible, because the gas or gas mixture is fed in at the bottom of the reactor and it vertically ascends opposite the direction of gravity and the direction of flow. Furthermore, more precise control of the pulsation and consequently the mixing of the liquid, suspension or emulsion can be obtained because of that. The higher the gradient in the reactor, the greater the turbulence that can be achieved with the gas pulsation; the angle $\alpha$ of the reactor gradient should not be greater than 90°, preferably <10°, especially preferably <5°. A method that is efficient in terms of material and energy is made possible because of the use of gravity and buoyancy.

Moreover, the device described above is advantageous for the cultivation of micro-algae because an incessant mixing of the algae culture is ensured as a result of the pulsating feed-in of the gas or gas mixture and adequate illumination of the algae is made possible in the culture. Micro-algae concentrations that are higher compared to known photobioreactors in the range ≥7 g/l can be used because of that, which corresponds to an increase of over 40%.

In a further embodiment of the invention, the reactor has an arbitrary geometry; it is preferably designed to be round (polyhedral base) and as a special preference is designed to be a pipe and/or tube/double-tube reactor. The minimization of (flow) dead zones in the system is useful to minimize clinging material, which is why circular geometries, especially of the pumping systems, for instance in tubes, pipes or tube reactors/tube photobioreactors are used as a preference. This geometry also allows the flexible, tilted arrangement of the reaction system in an angle from $0°<\alpha<90°$, preferably $0°<\alpha<10°$, especially preferably $0°<\alpha<5°$ vis-a-vis the horizontal plane.

The solution as per the invention consequently involves a method for generating pulsations through the use of gases and/or gas mixtures with a high internal energy, especially in a compressed state, at least a partially condensed state or at least a partially frozen state. The internal energy of the gases or gas mixtures is used in the process to drive a diaphragm pump and therefore to generate a pulse. The pulsation brings about an intensive mixing of the liquid, suspension or emulsion via specifically generated turbulence with the fed-in gases or gas mixtures in the reaction area and prevents a settling of suspensions or the clinging of solid particles to the wall, for example. In so doing, the energy of the compressed, condensed and/or frozen gas that is employed is used in an optimal way in terms of materials and energy management by simultaneously or separately providing the liquid transport, the generation of flows/turbulence via pulsations, a cooling capacity and also the reactants through the gas/gas mixture that is employed. The above-mentioned pulsation effect can be strengthened if the liquid is likewise transported in a pulsating fashion, e.g. with a diaphragm pump, when the gas is fed in.

Gases or gas mixtures with a high internal energy, i.e. in a compressed, (partially) condensed and/or (partially) frozen state are to preferentially be used in this procedure. The type of gas will, in particular, depend on the reaction to be carried out, availability, price, material compatibility and the like; in principle, though, any gas/gas mixtures can be used.

The gas quantity will, for instance, depend on the air consumption of the diaphragm pumps (pump lift, pumped volume, desired density differences between the phases, settling behavior etc.), on the equilibrium conditions (concentration for the reaction/solubility, pH value, reactivity or reaction speed) and on the turbulence desired via the targeted pulsation of the gas in the (reaction) solution.

There are no limitations in general with regard to the reactor; any geometries of the reactor or of the pumping system can be chosen. The minimization of (flow) dead zones in the system is useful to minimize clinging material, which is why circular geometries, especially of the pumping systems, for instance in tubes or tube reactors/tube photobioreactors are used as a preference. In accordance with the invention, the gas is fed in from the bottom of the reactor; that is why an ascending direction of flow vis-a-vis the horizontal plane is necessary.

In a further embodiment of the invention, the photobioreactor is designed in the form of a tube or double-tube reactor; the tubes are transparent or translucent and are preferably made of a flexible material. This is especially advantageous because possible stress on the material as a result of the pulsation can be avoided via the flexible design of the tubes. The tubes are preferably made of a flexible polymer, for instance PET. The transparent or translucent design of the tubes is essential here to ensure the cultivation of the phototrophic microorganisms.

In a further embodiment of the invention, the photobioreactor has a truncated-cone-shaped core structure and one or more transparent or translucent tubes, which are helically wrapped around the outside and/or the inside of the core structure. The transparent or translucent tube is comprised of at least two chambers, at least one of which has a cultivation medium flowing through it and at least one of which has a heat-exchange medium flowing through it. In contrast to the airlift principle, there is no gas distribution as per the invention; instead, a bubble is fed in through a pressure burst, for instance via a solenoid valve without a distributor device, which brings about the scenario described below in combination with the tilted position of the reactor and the flow velocity of the liquid.

In a further embodiment of the invention, a directly controlled solenoid valve is used to feed in the gas and a gas burst that is not finely distributed is generated with the aid of it.

The method described above can be used in a versatile and universal way in a number of technical areas, e.g. wherever liquids/reaction media/suspensions have to be pumped, where gases have to react with them or be dissolved and where heat (radiating in from the outside) has to be carried off in exothermal reactions/solutions of gases or gas mixtures.

Description of the Pulsation Effect

The generation of turbulence in the reaction solution or suspension as per the invention is to be described below with the aid of FIG. 1. In so doing, the liquid, suspension or emulsion is conveyed in a pulsating fashion by means of a diaphragm pump through a pipe or tube system that is arranged to be tilted at an angle α vis-a-vis the horizontal plane (1). Additionally, a gas or gas mixture is fed in at the bottom of the reactor, pipe or tube system. The gas pressure and the gas quantity depend on the bursting pressure of the reactor, the degree of contamination and/or the content of solids in the liquid, suspension or emulsion (2). The gas bubbles that are fed in move slowly in the direction of flow and in the upper part of the pipe or tube system. The flow velocity of the liquid increases under the gas phase because of the cross-sectional narrowing (3). A gas bubble arises in the pipe or tube system because of the continual replenishment of gas; the flow velocity of the liquid is high over a fairly large section (4-7). When a sufficient amount of gas has accumulated, a gas blockage arises and the liquid is no longer transported for a short period of time (8). If the counterpressure of the liquid is too high, the liquid abruptly flows back into the gas-filled area. The high flow velocity and the numerous small gas bubbles bring about very heavy turbulence. Solids clinging to the wall are dissolved and particles that have settled are whirled up again (9). After a larger gas bubble has formed from the small gas bubbles (10), the process starts up once again in a different place along the direction of flow (see Step 2).

As per the invention, this process of adding gas in a targeted, pulsating fashion to a liquid being pumped in a pulsating fashion can be efficiently used both to prevent the settling of suspensions or to prevent material from clinging to the reactor/pipe/tube wall and to clean it. The above-mentioned technique is therefore suitable for both a prophylactic/preventive cleaning and for a subsequent cleaning of systems or system parts.

In a further embodiment of the invention, carbon dioxide is used as the gas.

In a further embodiment of the invention, compressed, condensed and/or frozen carbon dioxide is used in reactors, preferably in bioreactors.

The methods and devices described above are equally applied in liquids, suspensions or emulsions. If only one of the terms is used in the description, that does not represent an explicit limitation, but merely a sample listing that is supposed to also include the other terms.

The precise adjustment of the parameters for the quantity of gas fed in, the flow velocity of the liquid, suspension or emulsion and the gradient angle of the tubes of the reactor is essential for the development of the pulsation effect; an optimal point among the flow velocity of the liquid, the quantity of gas fed in and the lead angle of the reactor is to be set in dependence upon the individual parameters.

Solutions to the problem can also involve a combination of the embodiments described above with one another in useful ways.

BRIEF DESCRIPTION OF THE DRAWINGS

The invention is to be explained in more detail below with the aid of a few examples and the accompanying figures. The examples are supposed to describe the invention without limiting it to them.

DETAILED DESCRIPTION OF THE PREFERRED EMBODIMENT

Figure 1:
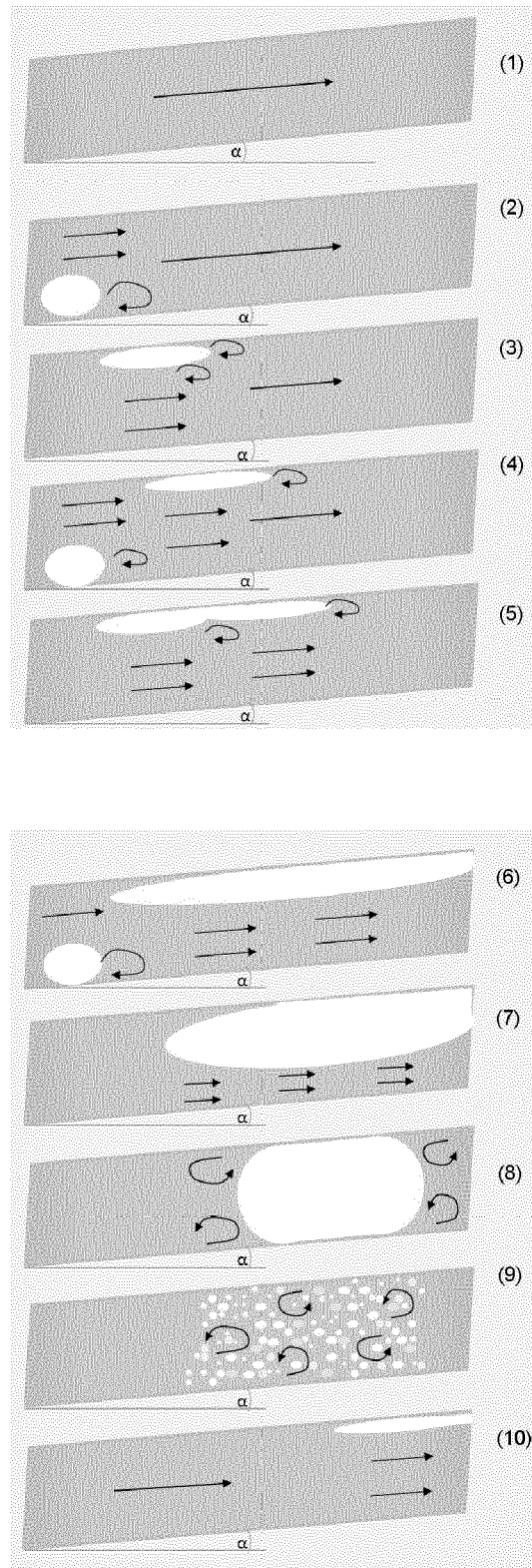
FIG. 1 shows a schematic diagram of the pulsation effect in a tube reactor
Figure 2:
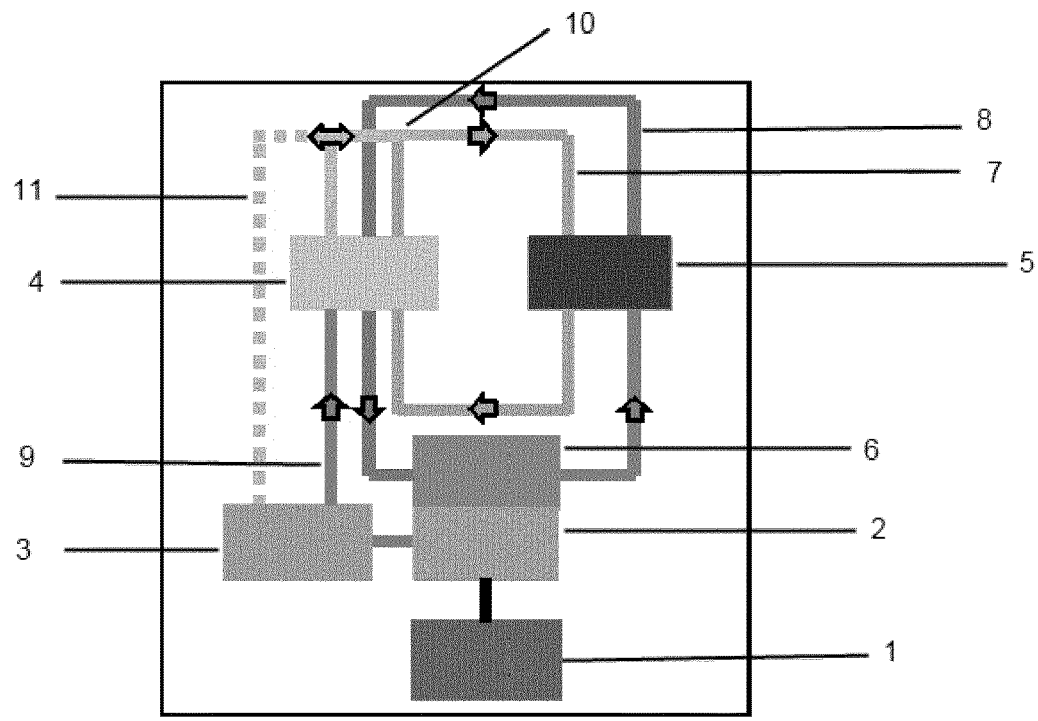
FIG. 2 shows a process flow chart for the use of compressed/condensed gases

In a first example, the system is comprised, in accordance with the process flow chart shown in FIG. 2, of a feeder tank 1, an evaporator unit 2 with a heat exchanger 6, a storage tank 3, diaphragm pumps 4 for the reaction solution 7 and a heat transfer medium 8, as well as the reactor 5. A gas metering unit 9 and a return line 11 are provided behind the diaphragm pump 4. The gas is fed into the reaction solution 7 via a feed unit 10 that is not shown in more detail.

Figure 3:
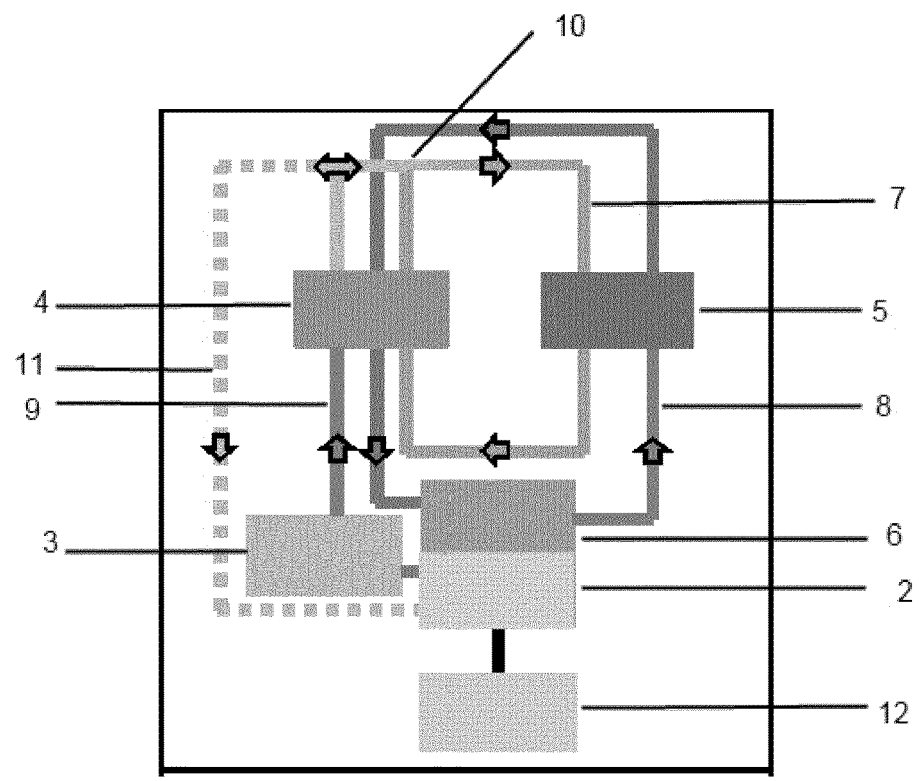
FIG. 3 shows a process flow chart for the use of frozen gases, e.g. dry ice

A process flow chart analogous to FIG. 3 is shown in FIG. 3 in a further example; the feeder tank 12 contains dry ice that is heated in a $CO_2$ evaporator 2, wherein the $CO_2$ evaporator 2 is connected to a heat exchanger 6 and there is cooling of the heat transfer medium 8 and therefore the reaction solution 7 in the reactor 5. Furthermore, the $CO_2$ is stored in a storage tank 3 and brought into the reaction solution 7 by means of the diaphragm pumps 4 through a feed unit 10 that is not shown in more detail. As per the invention, the reaction solution 7 is fed in a pulsating fashion, so turbulence is generated in the reaction solution 7 that also prevents solids from clinging to the reactor wall in addition to thoroughly mixing the reaction solution. Moreover, a return line 11 is provided that leads from the diaphragm pump 4 to the $CO_2$ evaporator 2.

The process takes place at every point in the pipe or tube system with a uniform geometry, but the pipe/tube cross-section, the flow velocity, the pulsation and the quantity of gas that is fed in are to be individually adapted to the system. The above-mentioned effect can be observed with a pipe cross-section of 42 mm, a flow velocity of the liquid of 0.45 m/s (2 $m^3/h$), a pulse frequency of the diaphragm pump of 2 Hz and a fed-in gas quantity of approximately 100 ml/10 s.

In a further example, a comparative test with a micro-algae concentration over 7 g/l was carried out in a customary tube photobioreactor; even a doubling of the flow velocity in the pipe/tube system was not able to prevent settling. In contrast, setting or clinging effects were not observed with the use of gas-liquid pulsation and half of the flow velocities.

A procedure that is extremely efficient in terms of energy and material results from the above-mentioned effects preventing clinging/settling of suspensions with a significantly lower flow velocity.

In a further example, additional optimization was achieved when a gas-material circulation system was developed (cf. FIGS. 2 and 3). The use of the high internal energy of the compressed, (partially) liquefied or (partially) frozen gases or gas mixture that is employed is decisive. The gas is cooled because of its adiabatic expansion, whereby cooling water can be cooled, for instance. The expanded gas (p>1.5 bar) is now used to operate the diaphragm pumps, which pump both the liquid/suspension/emulsion and the cooling water through the reactor. The gas (p>1.0 bar) that is expelled from the diaphragm pumps is now added to the liquid in a pulsating fashion in a defined quantity and at a defined point in time. Not only an efficient material circulation system (the gas conveys the liquids/suspensions/emulsions/cooling water, generates turbulence because of the pulsing input, takes part in the reaction etc.), but also an optimal use of energy (cooling of the cooling water via the expansion of the gas) is thereby obtained with the available resources.

Figure 4:
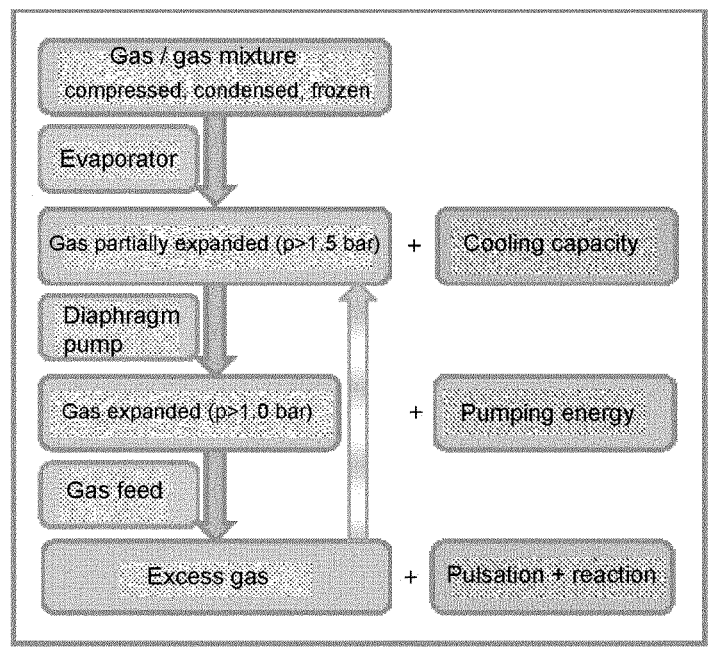
FIG. 4 shows a qualitative energy flow chart.

In a further example, the way in which the gas/gas mixture changes its internal energy in the process circulation system is schematically shown in FIG. 4. In the process, the gas or gas mixture first has a high internal energy because it exists in a compressed, condensed or frozen form. The gas or gas mixture is then added to the process circulation system through an evaporator 2 and partially expands. The temperature is lowered with this expansion via the cooling of the gas or gas mixture during the transition from an area of high pressure to an area of low pressure; this is used for cooling in accordance with the invention. The gas or gas mixture is then added to the reaction solution 7 via the diaphragm pump 4 and the feed unit 10, where turbulence is generated (Re>2300) due to the pulsing input as per the invention, which leads to a thorough mixing of the reaction solution 7 and to material being prevented from clinging to the walls. Moreover, the fed-in gas or gas mixture can be added to the reaction solution 7 as a reactant, where in can be converted into a product such as biomass in a reaction. In addition, the internal energy of the gas or gas mixture is separately used in an advantageous way, but preferably in a combined manner in a material and energy circulation system in the form of combined heat and power generation. Combined heat and power generation refers here to the generation of mechanical work to operate the diaphragm pumps 4 and the use of the evaporation/expansion heat from the expansion of the gas or gas mixture that is used.

Figure 5:
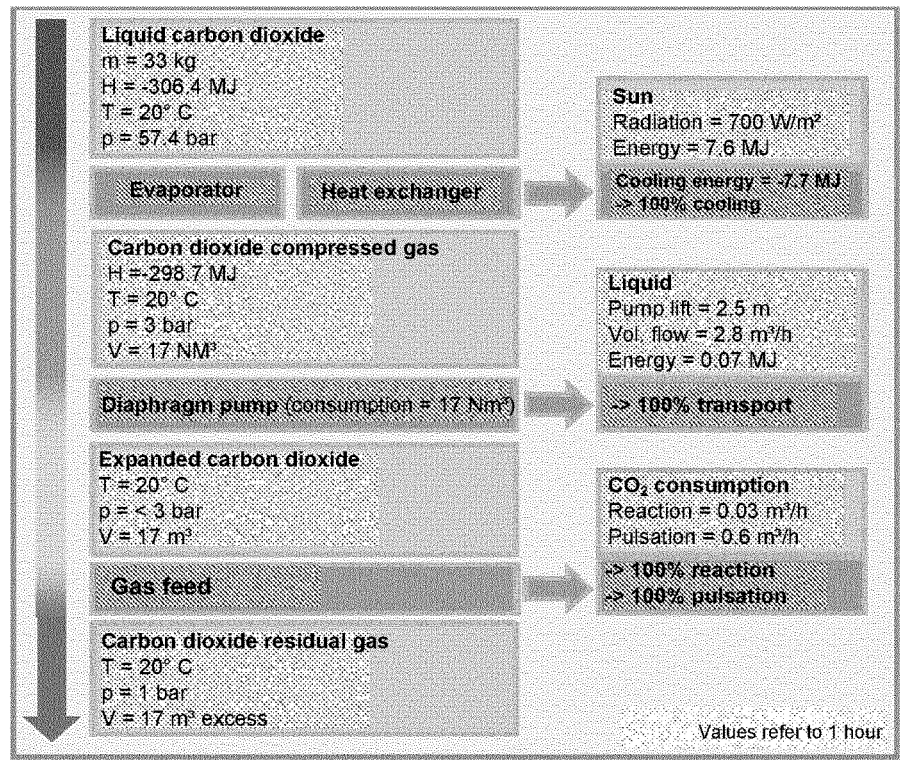
FIG. 5 shows a quantitative energy chart for the use of liquid carbon dioxide.

In a further example, sample values for the feed-in of carbon dioxide that are achieved with the method as per the invention are shown in FIG. 5; the values that are shown refer to values per hour.

In a further example, the pulsation effect was tested with a device that serves to cultivate micro-algae. The device is comprised of a photobioreactor that is designed to have a truncated-cone shape and a height of approximately 2.0 m. The diameter of this truncated-cone-shaped photobioreactor is approx. 2.5 m at the bottom and approx. 1.5 m at the top; it is made of silicone and comprised of a translucent, helically wound, double-tube system with a tube diameter of approx. 50 mm, tube spacing of approx. 35 mm, a length of approx. 150 m with a photoactive volume of approx. 200 l. Furthermore, the device includes a sensor station to determine the pH value, the optical thickness, the temperature, the $CO_2$ content and a flow-measurement unit, a storage container with a volume of approx. 200 l, a pumping unit with a centrifugal/diaphragm pump and connecting pipelines made of PE. The gases that are fed into the reactor can be metered in at the storage container, at the bottom of the reactor or in the connecting pipeline system via valves. The flow velocities of the suspension are in the range of 0.35-0.50 m/s.

In a further example, the device described above is used in normal operation without pulsation. It turned out here that the initial deposits were able to be observed on the light-entry surfaces of the PE tubes starting at a biomass dry weight concentration of 3-4 g/l. When silicone tubes are used, the silicone as the tube material prevents biofouling to a certain extent, so the initial deposits can first be observed starting at 6-7 g/l of biomass dry weight. No further micro-algae growth occurs because light is lacking for the photosynthesis at the corresponding concentrations stated above. After a successful harvest, the reactor is cleaned with hydrogen peroxide, for instance; the cleaning time was 4-6 days regardless of the tube material that was used.

In a further example, the device described above was used with pulsation. The micro-alga *Scenedesmus rubescens* was cultivated for 20 days for that. The biomass dry weight and the nutrient content of the suspension were measured on a daily basis. Nutrients were once again added starting at a biomass dry weight concentration of around 5 g/l (after approximately 1 week), and the pulsation (pulse time 1 s, pulse frequency 3 s, pulsation duration 10 min/h) was switched on until a maximum concentration of approx. 9 g/l was reached after a total of 14 days. After that, the micro-algae were separated out via a separator.

In the process, it turned out that the micro-algae productivity was in line with the expected growth rate in the 1st week at approx. 0.5 g/l/d. Whereas the productivity with micro-algae concentrations of around 5-6 g/l had therefore stagnated after around 1 week when the pulsation principle was not applied, or biomass was even consumed in the subsequent period, no drop in productivity was registered when pulsation was used up to concentrations of around 9 g/l of biomass dry weight.

It also turned out here that significantly higher final concentrations of the biomass dry weight (+30%) were able to be achieved due to the minimization of the bio-film buildup because of the use of the pulse technique. With regard to the subsequent solid-liquid separation to obtain the micro-algae, it can be carried out in a significantly more efficient way because of these higher concentrations of solids. Since the separation of the micro-algae from the suspension is a significant cost factor, the pulsation technique offers the possibility of economical micro-algae production on an industrial scale.

In a further example, the cultivation described above was carried out without pulsation. After that, the device was cleaned. In so doing, the complete micro-algae suspension was first removed and the device was filled with an approximately 3% hydrogen peroxide solution. The biomass that was still in the device and on the tube walls was killed off because of that. Stubbornly clinging bio-film was only removed from the walls with the use of the pulsation technique (pulse time 1 s, pulse frequency 3 s, pulsation duration 30 min/h). As a result, the device was ready for operation against after around 3 days.

In a further example, the cultivation described above was carried out with pulsation. When the device was subsequently cleaned, it turned out that the cleaning time of the tube-photobioreactor system was reduced by up to 50% because of the use of pulsations, and the system availability was therefore able to be correspondingly increased.

The invention claimed is:

1. A method for feeding gases or gas mixtures into a flowing liquid, suspension or emulsion in a reactor in a specific manner, characterized in that the gases or gas mixtures are fed with a specific amount and/or at defined points in time into a flowing liquid in a reactor system with a tube with an angle vis-à-vis the horizontal plane of between 0 and 90 degrees in one burst in the form of a gas bubble causing a pulsation effect, wherein a propulsive force is created by means of an adiabatic expansion of the gases or gas mixtures preventing material from clinging to the walls of the reactor, wherein the flowing liquid, suspension or emulsion that is conveyed is cooled because of the complete or partial use of the internal energy of the gases or gas mixtures and wherein the adiabatic expansion of the gases or gas mixtures is used to operate a diaphragm pump.

2. The method according to claim 1, characterized in that the flowing liquid, suspension or emulsion is conveyed in a pulsating fashion.

3. The method according to claim 1, characterized in that gases or gas mixtures with a high internal energy are used.

4. The method according to claim 3, characterized in that the gases or gas mixtures that are used are compressed, at least partially condensed or at least partially frozen.

5. The method according to claim 2, characterized in that the liquid is conveyed in a pulsating fashion because of the complete or partial use of the internal energy of the gases or gas mixtures.

6. The method according to claim 1, characterized in that the gases or gas mixtures, after being fed into the flowing liquid, suspension or emulsion, are partially or completely transformed in the flowing liquid, suspension or emulsion and/or dissolved in the flowing liquid, suspension or emulsion.

7. The method according to claim 1, characterized in that the gases or gas mixtures are fed into a photobioreactor with micro-algae.

8. The method according to claim 1, characterized in that the gases or gas mixtures include carbon dioxide.

9. The method according to claim 1, characterized in that the gas or gas mixture is fed in from the bottom of a photobioreactor and ascends vertically through the flowing liquid, suspension or emulsion against the direction of gravity and the direction of flow of the flowing liquid.

10. The method according to claim 1, characterized in that the amount of gases or gas mixtures fed in is 0.00-1.00 liter/s.

11. The method according to claim 1, characterized in that the flowing liquid, suspension or emulsion is pumped against the force of gravity at 0.35-0.50 m/s.

* * * * *